United States Patent
Sutherland et al.

(10) Patent No.: US 11,426,100 B1
(45) Date of Patent: Aug. 30, 2022

(54) BLOOD GLUCOSE TREND METER

(71) Applicant: Socrates Health Solutions, Inc., Dallas, TX (US)

(72) Inventors: Douglas F. Sutherland, Luxembourg (LU); Scott J. Smith, Dallas, TX (US)

(73) Assignee: Socrates Health Solutions, Inc., Dallas, TX (US)

( * ) Notice: Subject to any disclaimer, the term of this patent is extended or adjusted under 35 U.S.C. 154(b) by 14 days.

(21) Appl. No.: 15/363,983

(22) Filed: Nov. 29, 2016

Related U.S. Application Data (60) Provisional application No. 62/264,374, filed on Dec. 8, 2015.

(51) Int. Cl.
*A61B 5/145* (2006.01)
*A61B 5/00* (2006.01)

(52) U.S. Cl.
CPC ........ *A61B 5/14532* (2013.01); *A61B 5/7275* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 3,724,957 A | 4/1973 | Tamate et al. | |
| 4,014,321 A | 3/1977 | March | |
| 4,490,037 A | 12/1984 | Anagnostopoulos et al. | |
| 4,531,414 A | 7/1985 | Kraus | |
| 4,699,514 A | 10/1987 | Schmidt et al. | |
| 4,700,380 A | 10/1987 | Ahuja | |
| 4,901,728 A * | 2/1990 | Hutchison | A61B 5/14558 356/368 |
| 4,902,884 A | 2/1990 | Szabo et al. | |
| 5,009,230 A | 4/1991 | Hutchinson | |
| 5,383,452 A | 1/1995 | Buchert | |
| 5,398,681 A | 3/1995 | Kupershmidt | |
| 5,424,545 A | 6/1995 | Block et al. | |
| 5,477,327 A | 12/1995 | Bergman | |

(Continued)

FOREIGN PATENT DOCUMENTS

| CN | 102755167 A | 10/2012 |
|---|---|---|
| DE | 102009020701 A1 | 11/2010 |

(Continued)

OTHER PUBLICATIONS

International Search Report dated Nov. 22, 2013 in corresponding PCT application PCT/US13/65228, 2 pages.

(Continued)

*Primary Examiner* — Eric J Messersmith
(74) *Attorney, Agent, or Firm* — Foley & Lardner LLP (57) ABSTRACT

A system for obtaining and outputting real time blood glucose values or one or more indicators related thereto is described. The system comprises a sensor for obtaining blood glucose data from an individual in real time. The system includes an analyzer for comparing in a first comparison some or all of the blood glucose data obtained in real time and for generating an indicator in real time when the analyzer in comparing some or all of the blood glucose data identifies blood glucose data as unacceptable, the indicator provided as output on the user interface in real time.

17 Claims, 3 Drawing Sheets

(56) References Cited

U.S. PATENT DOCUMENTS

| | | | |
|---|---|---|---|
| 5,497,772 A * | 3/1996 | Schulman | A61B 5/14865 600/347 |
| 5,823,966 A * | 10/1998 | Buchert | A61B 5/14532 600/473 |
| 5,896,198 A | 4/1999 | Chou et al. | |
| 6,006,119 A | 12/1999 | Soller et al. | |
| 6,016,435 A | 1/2000 | Maruo et al. | |
| 6,370,407 B1 | 4/2002 | Kroeger et al. | |
| 6,567,678 B1 | 5/2003 | Oosta et al. | |
| 6,615,061 B1 | 9/2003 | Khalil et al. | |
| 6,708,048 B1 | 3/2004 | Chance | |
| 6,775,564 B1 | 8/2004 | Peters et al. | |
| 6,927,853 B2 | 8/2005 | Geiler et al. | |
| 7,245,952 B2 | 7/2007 | Cameron | |
| 7,248,905 B2 | 7/2007 | Fukuda et al. | |
| 7,253,899 B2 | 8/2007 | Shulman | |
| 7,299,079 B2 | 11/2007 | Rebec et al. | |
| 7,801,581 B2 | 9/2010 | Diab | |
| 7,964,806 B2 | 6/2011 | Freydank et al. | |
| 8,180,422 B2 | 5/2012 | Rebec | |
| 8,452,360 B2 | 5/2013 | Mandelis et al. | |
| 8,743,355 B2 * | 6/2014 | Korman | G01N 21/21 356/39 |
| 8,912,725 B2 | 12/2014 | Ye | |
| 9,101,308 B2 | 8/2015 | Korman | |
| 9,320,463 B2 | 4/2016 | Korman | |
| 9,330,237 B2 * | 5/2016 | Cohen | G06F 19/3456 |
| 9,636,052 B2 | 5/2017 | Korman | |
| 9,759,714 B2 | 9/2017 | Bordelon et al. | |
| 10,006,859 B2 | 6/2018 | Ashrafi | |
| 10,067,054 B2 | 9/2018 | Korman | |
| 2002/0106709 A1 * | 8/2002 | Potts | A61B 5/14532 435/14 |
| 2002/0187533 A1 | 12/2002 | Mross et al. | |
| 2003/0050541 A1 * | 3/2003 | Wuori | A61B 5/14532 600/316 |
| 2003/0137650 A1 | 7/2003 | Fine et al. | |
| 2004/0070754 A1 | 4/2004 | Schuster et al. | |
| 2004/0238361 A1 | 12/2004 | Shulman | |
| 2005/0054907 A1 * | 3/2005 | Page | A61B 5/0095 600/316 |
| 2005/0128482 A1 | 6/2005 | Gibbs | |
| 2006/0079762 A1 | 4/2006 | Norris et al. | |
| 2007/0016381 A1 * | 1/2007 | Kamath | A61B 5/14532 702/19 |
| 2007/0177162 A1 | 8/2007 | Glueck | |
| 2008/0117420 A1 | 5/2008 | Scarpaci | |
| 2008/0201095 A1 * | 8/2008 | Yip | G01N 21/274 702/85 |
| 2011/0105868 A1 | 5/2011 | Westphal | |
| 2014/0058220 A1 * | 2/2014 | LeBoeuf | A61B 5/0059 600/301 |
| 2014/0104596 A1 | 4/2014 | Korman | |
| 2014/0268103 A1 | 9/2014 | Korman | |
| 2015/0157246 A1 | 6/2015 | Leszinske | |
| 2015/0190100 A1 * | 7/2015 | Fox | A61B 5/746 340/539.12 |
| 2015/0342507 A1 | 12/2015 | Korman | |
| 2016/0022178 A1 | 1/2016 | Wang | |
| 2016/0209396 A1 * | 7/2016 | Bordelon | A61B 5/1455 |
| 2016/0317070 A1 * | 11/2016 | Sivaraman | A61B 5/14532 |
| 2017/0172480 A1 | 6/2017 | Braig et al. | |

FOREIGN PATENT DOCUMENTS

| | | |
|---|---|---|
| EP | 0 306 10 A1 | 6/1981 |
| EP | 0030610 A1 | 6/1981 |
| JP | 2005265592 A | 9/2005 |
| WO | WO-200060350 A2 | 10/2000 |
| WO | WO-0122871 A1 | 4/2001 |
| WO | WO-2014/062795 A1 | 4/2014 |
| WO | WO-2015/169955 | 11/2015 |

OTHER PUBLICATIONS

Written Opinion dated Nov. 22, 2013 in corresponding PCT Application No. PCT/US2013/065228; 6 pages.

Supplementary European Search Report for corresponding EP Patent Application No. EP13846901 dated Apr. 29, 2016, 10 pages.

Kozaitis, et al., "Laser Polarimetry for Measurement of Drugs in the Aqueous Humor," Annual International Conference of the IEEE Engineering in Medicine and Biology Society, vol. 13, No. 4, 1991, pp. 1570-1571.

International Search Report dated May 29, 2018 in PCT Application No. PCT/US18/29138, 4 pages.

International Search Report and Written Opinion for International Patent Application No. PCT/US2019/064005 dated Mar. 2, 2020.

International Preliminary Report on Patentability for PCT/US2019/064005 dated Jul. 15, 2021.

Non-Final Office Action on U.S. Appl. No. 16/045,450 dated Jun. 19, 2020.

Non-Final Office Action on U.S. Appl. No. 16/045,450 dated Jan. 28, 2020.

Anonymous: "Op Amp Input Offset Voltage," Analog Devices MT-037 Tutorial, Jan. 1, 2009; URL:http://www.analog.com/media/en/ training-seminars/tutorials/MT-037.pdf.

Extended European Search Report for EP 20176619.3 dated Aug. 24, 2020.

Notice of Allowance on U.S. Appl. No. 16/045,450 dated Sep. 22, 2020.

* cited by examiner

BLOOD GLUCOSE TREND METER

CROSS-REFERENCES TO RELATED APPLICATIONS

This application claims the benefit of and priority to U.S. Provisional Patent Application No. 62/264,374, filed on Dec. 8, 2015, and is incorporated herein by reference in its entirety.

STATEMENT REGARDING FEDERALLY-SPONSORED RESEARCH OR DEVELOPMENT

Not applicable.

BACKGROUND

The inventions as described herein relate to a device, system and method for blood glucose monitoring. The device and system include a blood glucose reading device and/or blood glucose information management system for utilizing said device, including monitoring, in real time, one or more blood glucose values so as to enable a user or others to determine one or more current glucose levels and/or trends of said glucose levels. The devices and systems described herein enable a user (or other person reviewing or monitoring the information, including the one or more levels and/or trends) to take appropriate action, such as to avoid and/or correct abnormal glucose levels.

Current spot blood glucose meters operate by taking a spot test of only one blood glucose value at a specific point in time or by taking continuous measurements of blood glucose over time. The current devices have several limitations. For example, spot test meters provide only one reading, which may or may not be an anomaly. Said single reading provides no basis as to whether the reading is accurate, is a technical error or is taken from a contaminated sample. In addition, when there may be concern about said reading and a second reading is taken, the second reading is taken some time later and the second reading provides no indication as to whether the second reading is actually a rise in blood glucose or whether the second reading is actually a drop in blood glucose (e.g., there is no indication as to whether the reading is obtained during a rise or during a rapid fall in blood glucose).

With current continuous blood glucose meters, the meters must rely on algorithms to smooth out noise due to wide reading fluctuations and generally rely on much less accurate and sometimes inaccurate information because current continuous readers in the market place have technical and design limitations that limit their accuracy. Most continuous blood glucose meters do not actually measure glucose in the blood but rather the glucose in the subcutaneous skin, and, therefore, exhibit a lag in providing actual blood glucose values, and are also prone to provide false and/or inaccurate readings. In the present marketplace, persons with diabetes continue to find continuous blood glucose meters to be inaccurate, generating false reading, and being unable to provide continuous accurate readings, particularly when blood glucose values are fluctuating. Most continuous blood glucose meters must be repeatedly calibrated by using a spot blood glucose meter and must be attached to the body in a manner that can be difficult to attach and keep attached and has been found to limit certain physical activities and/or contribute to psychological problems in some users. Due to the many limitations of current continuous blood glucose meters, the continuous meters include a disclaimer when the meters are purchased that state that a blood glucose test with a spot meter should be taken when adjusting medication or when undertaking a high risk activity, especially in moments of potentially rapid blood glucose level changes due to eating, insulin doses or strenuous physical activity meaning that the continuous blood glucose meters, alone, are not sufficient nor are they recommended for measuring blood glucose in such situations.

There remains a need for an improved device and a system that provides accurate blood glucose values in real time, while also providing further information about the blood glucose, such as the direction the blood glucose is taking (e.g., rising or dropping), as well as the rate of change in the blood glucose level. This need is growing due to the development of more rapidly acting insulin that can lead to more rapid changes in blood glucose levels. There remains a need for an improved blood glucose meter and systems utilizing said improved blood glucose meter to provide more reliable blood glucose readings and information related to said blood glucose reading in order to provide better blood glucose management decisions and medical dosing actions. There remains a need for improved blood glucose metering devices and systems utilizing said devices that are more efficient, user friendly, cost effective, and less complicated to use.

SUMMARY

The devices and systems described herein solve one or more of the issues or needs addressed above. The devices and systems utilizing said devices as described herein provide improvements to present blood glucose metering devices, including but not limited to improvements in providing blood glucose information to a user, or a person requiring or reviewing the blood glucose information. The information provided by the devices and systems described herein include but are not limited to providing one or more blood glucose values, one or more changes in blood glucose, one or more trends related to a plurality of blood glucose values, direction of trend of blood glucose values rate of movement of blood glucose values and direction of movement of blood glucose values.

The devices and systems described herein provide one or more blood glucose values, in which the values being provided are in real time, hence are rapid. The one or more blood glucose values are accurate. With more than one blood glucose value, said plurality of blood glucose values that are provided may be sequential, provided in one or more patterns, and/or used to provide one or more trends. The devices and systems described herein provide not only one or a plurality of blood glucose values, but are also capable of delivering information regarding a change in blood glucose, a rate in change in blood glucose, and/or a trend or pattern of blood glucose not found with alternative devices.

The devices and systems described herein for obtaining real time blood glucose values comprise, for example, a noninvasive sensor for obtaining blood glucose data in real time from an individual. The blood glucose data may be continuous data, sequential data and/or data obtained in one or more patterns. The device and system further comprises a controller. The controller includes a receiving unit for receiving the blood glucose data in real time. The controller includes a processing unit for processing some or all of the blood glucose data obtained in real time and for generating output, the output may be in one or a number of forms to be provided to a user. In one example, a sequence of blood glucose data (e.g., a predetermined sequence and/or pattern received by the controller) may be processed by the processing unit. In another example, all of the blood glucose data is received by the controller and is processed by the processing unit. In a further example, all of the blood glucose data is received by the controller and only a predetermined sequence and/or pattern is processed by the processing unit. Said data being processed by the processor will generate output. The controller includes a user interface having a display unit or other means for providing some or all of the output, as an executable result obtained from the processing unit. The controller is further configured to store at least some of the blood glucose data for some period of time. The processing unit is further configured to obtain at least some of the stored data. In one or more embodiments, the processing unit obtains data sequentially. In one or more embodiments, the processing unit processes some or all of the obtained data sequentially, maintaining said sequence when providing the executable result. In one or more embodiments, the processing unit obtains stored data sequentially, maintaining said sequence when providing the executable result. An indicator and/or an alert generated in relation to some or all of processed output may also be provided. The indicator and/or an alert may include information provided locally or transmitted wirelessly (via email, text, phone or otherwise) to a user. The user may be person from whom the real time blood glucose values were obtained. The user may be a third-party who is, for example, reviewing the information, monitoring the device and system, etc.

In one or more embodiments are described a blood glucose metering device and systems and methods of use, the device receiving spot or noninvasive sample data as accurately representing blood glucose data, the device further processing some or all of said sample data, and storing and/or providing information from or related to said sample data. In one example, information is provided as a blood glucose change and/or a blood glucose trend. Sample data received by the device is representative of blood glucose data from an individual. A reading device may receive the sample data and associate the sample data with a blood glucose value. A processing unit or device processes some or all of the sample data (received from a spot or noninvasive unit and/or from the reading device). A storage unit or device stores some or all of the sample data. A storage unit or device stores some or all of the processed data. Additional features of the blood glucose metering device include but are not limited to: converting at least a portion of the sample data and/or processed data into new information regarding blood glucose levels, blood glucose trends, changes in blood glucose levels, and/or changes in blood glucose trends; transmitting at least a portion of the sample data and/or processed data and/or said new information; triggering an event such as a communication, an indicator and/or an alert associated with and/or in response to some or all of the sample data and/or the processed data and/or said new information that is transmitted. The blood glucose metering device described herein provides or otherwise generates from the sample data one or a plurality of real time blood glucose values, one or more patterns from the plurality blood glucose values, and/or one or more trends related to said plurality blood glucose values.

In operation, each device described herein may also include an ability to perform or initiate sequential blood glucose spot or noninvasive sampling of an individual, to obtain the spot or noninvasive sample data accurately representing blood glucose data of the individual. Said performance or initiation may occur automatically or may arise on demand. In operation, each device described herein may obtain the spot or noninvasive sample data accurately representing blood glucose data of the individual in accordance with a test sequence or on demand. A test sequence is any sequence of sample data received. In one or more embodiments, the test sequence is in accordance with a set of predefined parameters.

The processing unit for a blood glucose metering device as described herein can perform a number of operations. For example, the processing unit can compare in real time (e.g., on demand or in accordance with a test sequence) blood glucose values (compare a new or a next value with, e.g., a previous value or a set value) and can generate a communication, an indicator and/or alert in real time (e.g., when the new or next value differs from the previous or set value or from any desired value, or in response to a certain change between two or more values, or in response to a certain trend of two or more values). The processing unit can run the test sequence (e.g., initiate and/or receive a sequence of sample data in accordance with predefined test parameters) in real time. The processing unit can start and stop during a testing sequence and can at any time (e.g., in accordance with a test sequence, or on demand) provide a blood glucose reading in real time. The processing unit can also run a number of test sequences, can set the number or frequency of running said test sequences, and/or set a period of time between test sequences (e.g., every 10 seconds, every 30 seconds, every minute, etc.). The processing unit can set or re-set a blood glucose test sequence after a period of time and/or based on a blood glucose value (e.g., re-sample and/or re-initiate sampling in order to receive new or next sample data representative of blood glucose in real time, said re-sampling and/or re-initiating may continue on demand or for some period of time after obtaining a new or next blood glucose level). The processing unit can in accordance with a re-sampling provide blood glucose level(s) and/or trend(s) for some period of time and/or at some periodic interval for some period of time and/or in accordance with achieving some set value. The processing unit can set a new test sequence and/or a new sampling based on detection of, determination of, or conversion of sample data that reflects a specified blood glucose value, a specified range of blood glucose values, a specified rate of change in blood glucose value, a specified trend of blood glucose values, and/or a directional change in the blood glucose value. In one or more examples, sampling may be continued for at least a period of time or until a new or next blood glucose value, or range of values, or rate of change of value, etc., is no longer of the same specified value, same specified range of values, same specified rate of change of value, etc. The processing unit may combine any of the information in any number of combinations to provide one or more blood glucose levels, rate of change of blood glucose levels, blood glucose trends, and/or re-initiate sampling. Thus, blood glucose values provided in real time may be provided at one or more pre-defined or specified times, in accordance with one or more specified test sequences (or some specified combination of test sequences, that may or may not be initiated by an anomaly or by a specified blood glucose value, specified rate of change in blood glucose value, and/or specified blood glucose trend).

In some embodiments, a test sequence may include an ability to perform or initiate sequential blood glucose spot or noninvasive sampling of an individual. In some embodiments, a test sequence includes receiving sample data from a spot or noninvasive unit.

The processing unit may also set a specific test sequence for some extended period via a repeater function (like an automatic snooze alarm) that will provide continued information and blood glucose values, thereby removing the requirement to establish or set another test sequence, and allowing sampling and/or receiving of sample data to continue automatically, without having to be reset. This provides an automated and extended trend capability. The processing unit can display trends over "one-off reading anomalies" within the trend (with ability to flag when this was done). The processing unit can display various information as output (e.g., glucose value, trend, test sequence, anomaly) in numerical and/or graphical displays. The processing unit can also provide a simple visual indicator for a value and/or trend via, for example, a directional arrow (e.g., up, down or flat).

A system for obtaining real time blood glucose values is provided. The system may include a reading device with a detection module including a noninvasive sensor configured to obtain blood glucose data in real time from an individual and generate sample data therefrom, and a monitoring module configured to receive sample data from the reading device and in response to provide a real-time output comprising at least one of: a single blood glucose value, a plurality of blood glucose values, a rate of change in blood glucose values, and a trend in blood glucose value, wherein the sample data is processed continuously.

In various embodiments, the output module provides continuous real-time output. Moreover, the output module may provide an indicator in response to one or more blood glucose values being outside a range of specified values. In various instances, the output module provides an indicator in response to a trend of blood glucose values exceeding a rate of change in glucose level specific for the user. Moreover, the system may also have a database storing relational data comprising an average rate of change of blood glucose over a fixed number of samples of the sample data.

A method of obtaining real time blood glucose values is provided. The method may include receiving sample data from a reading device by an indicator module of a monitoring module associated with the reading device, analyzing the sample data by comparing the sample data with at least one of a prior trend of prior sample data and a rate of change of the prior sample data, and indicating by the indicator module an alert in response to the analyzing step providing a blood glucose value outside an acceptable trend of blood glucose values and outside an acceptable rate of change of the blood glucose values.

These and other embodiments are further described below.

BRIEF DESCRIPTION OF THE DRAWINGS

For a more complete understanding of various embodiments of the present disclosure and the advantages thereof, reference is now made to the following brief description, taken in connection with the accompanying drawings, appendices, and detailed description, wherein like reference numerals represent like parts, and in which.

DESCRIPTION OF THE VARIOUS REPRESENTATIVE EMBODIMENTS

Described herein is a blood glucose monitoring system 5 for providing blood glucose values and alerts for an individual in real-time. In the embodiment illustrated in FIG. 1, the blood glucose monitoring system 5 includes a reading device 10 receiving initial sample data 20, and a monitoring module 30 for processing and/or converting at least some of the initial sample data 20 for output 90. The output 90 may be values representing blood glucose values. The output 90 is provided in real time. The monitoring module 30 may also or alternatively provide an indicator (e.g., a symbol, an alert, a number, a communication, a graphical representation, etc.) in real time. In some embodiments, initial sample data 20 includes amplified signals or information, digitized signals or information, subtraction signals or information, calibrated signals or information, colorimetric signals or information, etc., which are associated with or otherwise capable of being converted to or of representing blood glucose values. In some embodiments, initial sample data 20*a* is modified as modified sample data 20*b* for processing by the monitoring module. Initial sample data 20*a* may be modified by the reading device 10 or may be modified thereafter. In some embodiments sample data 20 received by the monitoring module may be modified sample data 20*b*. In some embodiments, sample data 20 received by the monitoring module may be or may represent blood glucose values, thereby having little or no need for modification. In some embodiments, initial sample data 20*a* is modified as modified sample data 20*b* by the monitoring module.

Figure 1:
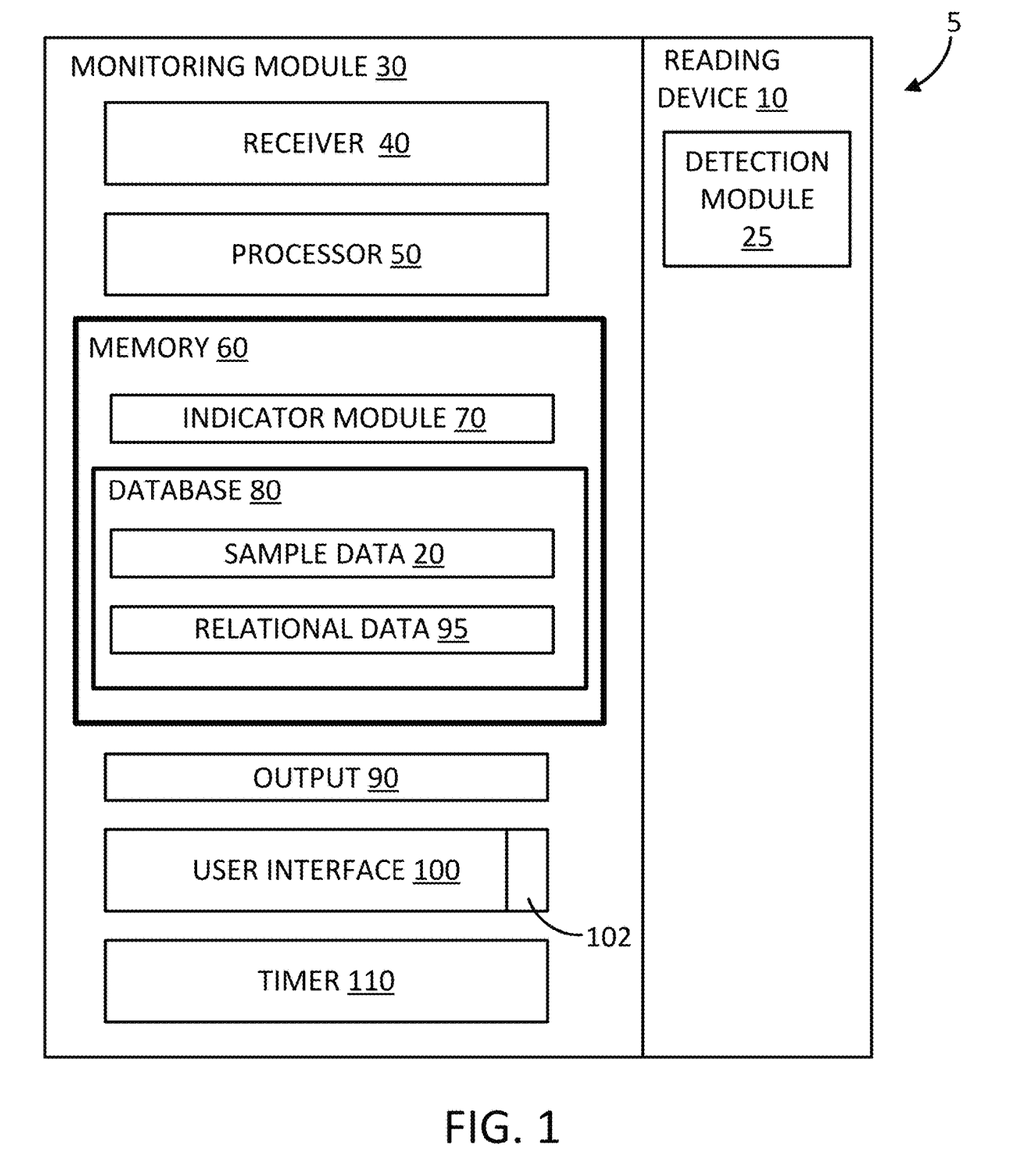
FIG. 1 is a representative schematic of a system described herein.

Processing by the monitoring module 30 may include but are not limited to converting or otherwise modifying the initial sample data 20*a* and/or modified sample data 20*b*, recording the initial sample data 20*a* and/or modified sample data 20*b* (in short term or in long term memory), transmitting output 90 based at least in part on one or more sample data 20 (20*a* or 20*b*), tagging or otherwise providing an indicator with a portion of the output 90.

In one or more embodiments, output 90 represents one or more blood glucose values and/or indicators related to the one or more blood glucose values. The output 90 may be similar or the same as sample data 20*a* or sample data 20*b*, representing a single blood glucose value, a plurality of blood glucose values. The output may include a rate of change in blood glucose values, and/or a trend in blood glucose values. An indicator may be associated with the single blood glucose value, one or more of the plurality of blood glucose values, one or more of the rate of change in blood glucose values, and/or one or more trends in blood glucose values. In some embodiments, an indicator is associated with the output 90 when a second or next or later output fluctuates from a first or prior or earlier output. The fluctuation may be outside a specified output value or outside a range of specified output values.

In one or more embodiments, a reading device 10 is a noninvasive device for obtaining blood glucose values or signals or data related to and for representation of blood glucose values, such as, for example, a sensor as described in U.S. Pat. No. 8,743,355 and U.S. Publication No. 20140268103, both of which are incorporated herein by reference in their entirety. The signals received from these reading devices may be electrical and/or optical signals. It should be understood, however, that alternative non-invasive devices may also be included and/or substituted as device 10 (e.g., a device that measures blood glucose by inhalation, by a pump, by pressure, etc.). In some embodiments, the reading device 10 is or further comprises a blood glucose meter or glucometer or spot test meter (e.g., blood glucose test strip device or blood glucose reagent/reaction device or blood glucose consumable device, which assesses blood glucose from a blood sample obtained from an individual). The signals received from these reading devices may be colorimetric and/or chemical. The reading device 10 may be portable and/or wearable. The reading device 10 may comprise a detection module 25 that receives and/or generates sample data 20 (or initial sample data 20*a*) in real time. Alternatively, a system 5, comprising the reading device 10 will include a detection module 25 receiving and/or generating sample data 20 (20*a* and/or 20*b*) in real time.

In operation, sample data 20 (representing one or more blood glucose values or modified as sample data 20*b* to represent one or more blood glucose values) is/are processed in real time by the monitoring module 30, providing a real-time output 90, the output being in the form of, for example, a single blood glucose value, a plurality of blood glucose values, one or more rates of change in blood glucose values, one or more trends in blood glucose values.

In some embodiments, the sample data 20 described above is processed continuously when provided to the monitoring module 30, and can provide continuous real-time output 90. In some embodiments, the sample data 20 described above is processed continuously when provided to the monitoring module 30, and can provide intermittent or variable real time output 90 (e.g., intermittent or having some variability due to a predefined or variable pattern or algorithm for transmitting output 90).

In some embodiments, the sample data 20 described above is processed on demand. In still additional embodiments, the sample data 20 described above is processed in accordance with a setting or test sequence, in which the test sequence may have a defined start time and/or a defined end time as well as defined sampling and/or processing pattern.

In some embodiments, the output 90, when fluctuating outside a specified value or outside a range of specified values, may be associated with an indicator. In some embodiments, an indicator is associated with the output 90 when or until or unless output 90 continues fluctuating for some period of time or for some number of fluctuations or for some specified range of fluctuations, or some combination thereof.

With the embodiments described, a glucose level trend specific for an individual can be established. In some embodiments, the trend may be used to set the fluctuations, e.g., the specified value and/or range of specified values that are utilized to determine when output, and hence when one or more blood glucose values fluctuate and are outside a specified value or outside a range of specified values (e.g., specified trend value(s)). The trend enables an individual to understand and receive an indicator in real time when one or more output values, and hence one or more blood glucose values, fluctuate to an extent requiring attention (e.g., when the blood glucose value is beyond an acceptable trend), so as to provide immediate, real-time information regarding medication, dosage, diet, and/or other medical issues before being the individual is adversely impacted by a more dramatic change in blood glucose level.

With the embodiments described, a rate of change in glucose level specific for an individual can be established. In some embodiments, the rate of change may be used to set the fluctuations, e.g., the specified value and/or range of specified values that are utilized to determine when one or more blood glucose values fluctuate outside a specified value or outside a range of specified values (e.g., specified rate of change value(s)). The rate of change enables an individual to understand and receive an indicator in real time when one or more output values, and hence one or more blood glucose values, fluctuate to an extent requiring attention (e.g., when the blood glucose value is beyond an acceptable rate of change of blood glucose), so as to provide immediate, real-time information regarding medication, dosage, diet, and/or other medical issues before being the individual is adversely impacted by a more dramatic change in blood glucose level.

In an embodiment such as one illustrated in FIG. 1, the reading device 10 receives and/or otherwise generates sample data 20, detection module 25 may be included for generating sample data 20 (and may modify said sample data as sample data 20*b*). Sample data 20 (20*a* and/or 20*b*) received by monitoring module 30 in real time. Sample data 20 may be received by the monitoring module 30 as a "batch" (i.e., a plurality of sample data 20 provided in series). The batch may include continuous sample data 20, an interval of sample data 20, and/or sample data 20 in a predefined sequence. In one or more embodiments, the sample data 20 are data samples obtained in series over a period of time. The period of time may be short. The period of time may include seconds, minutes, or over a series of seconds and/or minutes. The period of time may be repeated. In one embodiment, as illustrated in FIG. 1, the reading device 10 and the monitoring module 30 are a single integral unit. In some embodiments, the reading device 10 and the monitoring module 30 are separate or separable components communicatively coupled via a wired or wireless connection.

In the embodiment illustrated in FIG. 1, the monitoring module 30 includes a receiver or receiving unit 40 for receiving the sample data 20 from the reading device 10, a processor 50 for processing the sample data 20, a memory 60 for recording and storing (temporarily or permanently) some or all of the sample data 20 and/or processed sample data 20 and/or output 90, a user interface 100, and a timer or clock 110. The memory 60 may further comprises an indicator module 70 and a database 80 comprising any form of the sample data 20 and, as further described below, relational data 95.

The indicator module 70 may comprise hardware, software, or a combination of hardware and software. In FIG. 1, the indicator module 70 is illustrated as being stored in the memory 70 so as to be accessible and/or executable by the processor 50. However, it should be understood that some or all of the indicator module 70 may be otherwise stored, even remotely. In one operation, the indicator module 70 is used to analyze in real time sample data 20 received by reading device 10 (i.e., signals, blood glucose values, etc.), to determine in real time whether any one or more sample data, and hence, any one or more glucose level is trending too high or too low or has otherwise reached an undesired level based on prior sample data, or based on a series of prior sample data (e.g., prior trend), or based on a set value or a series of set values. The indicator module may also analyze output 90 in real time, such as when sample data 20 is modified as modified sample data 20*b* which is provided as output 90. The analysis may include relational data 95. The relational data 95 may further comprise a rate of change of blood glucose (e.g., rate of change between a new sample data 20*d* and a prior sample data 20*c*). The relational data 95 may further comprise an average change of blood glucose or an average rate of change of blood glucose (e.g., average of or average difference between sample data 20 (20*a* or 20*b*)

over some fixed period of time or with a fixed number of data samples). The analysis by indicator module 70 may be continuous, may be intermittent (by a predetermined setting) or may be on demand.

In one embodiment, data received from monitoring module 30 is analyzed by the indicator module 70 in a predetermined pattern, such as by a pattern defined by a test sequence. Data may also be analyzed continuously or on demand. In one or more embodiments, analysis includes simply analyzing a sample data against a previous sample data, in which the previous sample data does not have to be immediately previous but is previous as defined by some period of time. In some embodiments, analysis includes analyzing sample data against previous sample data and providing a corresponding percent change based on the two data sets. The percent change may be provided as relational data 95 and further evaluated against a previous percent change, or against a predefined percent change (e.g., a specified or acceptable value or range of values for said percent change). In some embodiments, analysis includes analyzing a sample data or a series of sample data against a previous sample data or series of sample data and providing a corresponding rate of change in the data. The rate of change may be provided as relational data 95 and further evaluated against a previous percent change, or against a predefined percent change (e.g., a specified or acceptable value or range of values for said percent change). In some embodiments, analysis includes analyzing a series of sample data against a previous series of sample data and providing a trend in the data. The trend may be provided as relational data 95 and further evaluated against a previous trend, or against a predefined trend (e.g., a specified or acceptable value or range of values for said percent change).

In any of the above described embodiments, or various alternatives, as would be understood by the description, the relational data 95 may provide an indicator in the event blood glucose value, a trend in the blood glucose value, or a rate of change in the blood glucose value is at or near an unacceptable or specified value (or is at or near some unacceptable or specified range of values). In addition, it is also understood that the relational data may provide an indicator when one or more blood glucose values are acceptable, or in an acceptable range of values.

Whether data, and hence blood glucose, is sampled and/or processed continuously, intermittently (e.g., in accordance with a test sequence), or on demand, the device and system described herein is designed with any one or more of the following capabilities:

provide a single blood glucose reading (providing a single blood glucose value, or output representing a single blood glucose value);

provide a plurality of blood glucose readings (providing a plurality of blood glucose values, or outputs representing the plurality of blood glucose values);

provide a plurality of blood glucose readings (providing a plurality of blood glucose values, or outputs representing the plurality of blood glucose values) continuously;

provide a plurality of blood glucose readings (providing a plurality of blood glucose values, or outputs representing the plurality of blood glucose values) in accordance with a test sequence, the test sequence having the capability of performing automatically while the device and system are in operation, or with a repeated test sequence, the test sequence automatically repeating indefinitely or for some set period of time;

provide on-demand blood glucose reading(s) (providing a single or plurality of blood glucose value, or output representing a single or plurality of blood glucose value), which can be performed at any time and/or during a test sequence;

provide a new test sequence when detecting one or more fluctuations outside a specified value or range of specified values, this may be an automatic function and always occurs based on certain and/or defined settings;

provide a blood glucose trend after some period of time and/or for a specific amount of time (e.g., in accordance with a test sequence, obtaining sample data representing blood glucose values for some period of time, such as every 5 minutes or every 10 minutes, and/or for some sequential pattern, such as every 1 minute for 10 minutes with a rest period for 50 minutes);

provide a rate of change of blood glucose after some period of time and/or for a specific amount of time (e.g., see example above);

provide one or both a blood glucose trend and/or a rate of change of blood glucose when output, representative of blood glucose values, change more than a fixed percentage;

repeat one or both of the providing of a blood glucose trend and/or a rate of change of blood glucose for some fixed period of time or in accordance with a test sequence when output, representative of blood glucose values, change more than a fixed percentage;

display one or a plurality of blood glucose readings on demand;

display one or both a blood glucose trend and/or a rate of change of blood glucose for some set period of time as well as an fluctuations therein, thereby, overshadowing single or intermittent abnormalities (such as by showing a directional arrow, up or down);

display brief, intermittent or single abnormalities within the display of the blood glucose trend and/or the rate of change of blood glucose, the brief, intermittent or single abnormalities;

display one or more blood glucose values or provide some alternative display or sound when the output value is within the acceptable value or acceptable range of values;

display one or more indicators (e.g., when output representative of blood glucose value(s) fluctuate(s) outside a specified value or outside a range of specified values, such as by showing a directional arrow, up or down); and display one or more indicators (e.g., when output representative of blood glucose value(s) fluctuate(s) are within a specified or acceptable value or within a range of specified or acceptable values).

In the event that it is determined that sample data 20 (20*a* or 20*b* or output 90) represents a glucose value that is outside of a predefined or specified value or specified range or range of specified values, indicator module 70 provides an indicator to the user interface 100. The indicator may be in any form, such as a symbol, light, sound, graphical display, number, text, e-mail, or some combination thereof. The indicator may be in a form suitable to notify an individual that the blood glucose level requires further monitoring. The indicator may, in some embodiments, initiate the indicator module 70 to analyze new sample data (received in real time), in which the new sample is analyzed by the indicator module 70 for some specified period and/or in some pattern in accordance with a specific test sequence.

Additionally and/or alternatively, in the event that the sample data 20 (20*a* or 20*b* or output 90) represents a glucose value that is trending in or towards a direction outside of a predefined or specified value or specified range or range of specified values, indicator module 70 may provide a same or different indicator to the user interface 100. The indicator may then initiate the indicator module 70 to analyze new sample data (received in real time), in which the new sample is analyzed by the indicator module 70 for some specified period and/or in some pattern in accordance with a specific test sequence. Providing an indicator to a user interface 100 prior to having a glucose level reach an undesired level may be critical in preventing the individual from having to seek medical attention, allowing the individual to instead address these lesser fluctuations in glucose level early and before reaching an undesired level.

In some embodiments, the user interface 100 includes a display 102 for displaying an output or alert to a user. In the embodiment illustrated in FIG. 1, the display 102 can be a liquid crystal display screen for displaying graphics and/or alphanumeric messages thereon (e.g., a symbol, a specific glucose number, an image, a message, and/or a text indicating that a glucose level is approaching or is in a danger zone, etc.). In other embodiments, the user interface 100 can include other types of visual indicators, such as one or more LEDs configured to flash or change colors. For example, in some embodiments, an LED can be configured to blink (flashing between an "on" and "off" condition) or change colors (change from green to red) in the event a glucose level is outside of a desired level or trending toward an undesired level. In other embodiments, the user interface 100 can be a speaker for providing an audible alert, such as, for example, a buzzer, beep, or other sound, or in the alternative, an audible message (prerecorded or otherwise) for providing an audible alert or message to the user of the system 5. In other embodiments, the user interface 100 is operable to generate an email message, a text message, a phone message, or any other type of message in order to send an alert to any desired recipient. Regardless of the type of user interface 100, the monitoring module 30, indicator module 70 and the user interface 100 are operable to, in one or more embodiments, provide real time indicators and/or real time alerts. The indicators and/or alerts may be provided to a user (e.g., via user interface 100), or to any other person monitoring the user (e.g., via a wired or wireless transmission). The indicators and/or alerts may be provided prior to a glucose level reaching an undesired value. Similarly, the indicators and/or alerts may be provided when the glucose level is at an acceptable value. With the system 5 described herein, monitoring module 30 is capable of recording and outputting the sample data 20 in real time.

According to some embodiments, the timer 110 is operable to allow the monitoring module 30 to receive and process each or a plurality of sample data 20 (new or next sample data) at a particular period of time, at a predetermined time interval, or any combination thereof. According to some embodiments, the timer 110 is operable such that the sample data 20 may be received by the monitoring module 30 and/or analyzed by the indicator module 70 at one or more regular intervals, such as in accordance with a test sequence. The test sequence may define the number of times sample data is received (e.g., every minute, every hour, every other hour, etc.) and/or during one or more predetermined time(s) during a day (e.g., from 8 am to 10 am and 12 pm to 2 pm, etc.) and/or one or more patterns (e.g., every other minute for 20 minutes). Additionally or alternatively, the sample data 20 may be received by the monitoring module 30 and/or analyzed by the indicator module 70 in response to an event. For example, when the sample data 20, relational data 95, or output 90 is a specified value.

In operation, each sample data 20 is a blood glucose value or is converted to blood glucose value or is converted to reflect a blood glucose value. In some embodiments, conversion may occur in the reading device 10 and before sample data 20 is received by monitoring module 30. In other embodiments, the raw sample data 20 is transmitted or otherwise provided to the monitoring module 30, where the sample data 20 may be converted to a blood glucose value or is process or converted to reflect a blood glucose value (e.g., modified sample data 20*b*). In some embodiments, sample data may also be processed in the indicator module 70, in which sample data 20 is processed and otherwise compared to a prior sample data or a set data value. The processing in any of the monitoring module 30 and the indicator module 70 may include amplification, filtering, averaging, subtraction, etc.

Additional analysis may be provided by the devices and systems described herein. For example, sample data 20 representing a blood glucose value received by monitoring module 30 may provide (reflect) at least a first blood glucose value and a second blood glucose value in a test sequence. The first and second blood glucose values may or may not be received with an interval there between. The first and second blood glucose values may be used to provide a set value, in which the set value is a range, or a trend or a percent change. The set value may then be used to compare against one or a plurality of further received sample data. When said further received sample data are within the set value, no indicator is initiated. When said further received sample data is outside the set value, an indicator is initiated. For example, an alarm may be generated. The alarm, when generated may include a visual indicator on a display. The alarm may be transmitted as a sound or vibration or any combination thereof. As previously explained, the alarm is generated. The indicator may reflect a rise in blood glucose, a drop in blood glucose, or an acceptable blood glucose.

According to embodiments disclosed herein, an indicator when generated is transmitted in real time, as, for example, a sound, a vibration, a visual indicator (e.g., light, image, on a display, etc.), and any combination thereof, in which there may also be a number of sounds, a number of different vibrations, a number of lights or colors, a number of images, etc. In some embodiments, the number of sounds or number of different vibrations or number of lights or colors, or number of images, as examples, may each be transmitted in relation to a specified indicator. As an example, an upward arrow may be visually displayed on a display panel 102 when a blood glucose value is trending upward, or when a rate of change of blood glucose values is positive. A horizontal arrow may be visually displayed on the same display panel 102 when a blood glucose value is acceptable (in an acceptable range). A downward arrow may be displayed on the same display panel 102 when blood glucose value is trending downward, or when a rate of change of blood glucose value is negative. Different colored lights or a different number of displayed lights could replace or be provided in addition to the upward, downward and horizontal arrows. Similarly or in combination, different beeps or different types of vibrations could be used.

Methods associated with the systems described herein include any one or more of the following and in no particular order:

providing an instantaneous normal or actual blood glucose reading, in which, for example, the real time blood glucose reading is or is from sample data 20;

providing and/or setting a blood glucose test sequence, which may occur, for example, automatically while a reading device 10 is in place or when the reading device 10 is in an active mode, in which sample data 20 is received and/or processed in accordance with parameters set by the test sequence, in which the test sequence may operate automatically or may be operate on-demand;

setting a blood glucose test sequence for a specific period of time (e.g., defining a start time, end time, and pattern of testing), in which during the test sequence both blood glucose levels and trends and/or rate of change or percent change of blood glucose levels are provided in accordance with the test sequence (e.g., sampling for 5 minutes, every 5, 10, or 15 minutes, etc. for one hour and every other hour thereafter);

starting and stopping a blood glucose test sequence, in which starting and stopping may occur, for example, in accordance with the test sequence or may be interrupted by an on-demand request for a blood glucose value;

generating an indicator during a test sequence when, for example, more than one blood glucose value is outside a trend;

providing and/or setting a frequency of processing and/or storing sample data in a test sequence (e.g., every 30 seconds, every minute, etc.);

providing a new test sequence having a same or different parameters, in which the new test sequence is initiated only when blood glucose value fluctuates outside an acceptable value, outside an acceptable percentage, outside an acceptable rate, and/or an outside acceptable trend, or some acceptable range thereof, in which an indicator is associated with said unacceptable fluctuations (or when near the unacceptable fluctuations);

analyzing for a rate of change in blood glucose in real time, some or all of which may be associated with indicator (e.g., when one or more blood glucose values are outside an acceptable value or range of acceptable values);

analyzing for a trend in blood glucose in real time, some or all of which may be associated with indicator (e.g., when one or more blood glucose values are outside an acceptable value or range of acceptable values);

analyzing for anomalies in a rate of change in blood glucose in real time;

analyzing for anomalies in a trend in blood glucose in real time;

providing a blood glucose value and/or a trend of blood glucose values;

providing a plurality of blood glucose values over a test sequence and automatically repeating the test sequence;

recognizing and/or displaying anomalies and/or abnormalities within a trend (e.g., providing an indicator in relation to an anomaly and abnormality);

displaying blood glucose values numerically and/or graphically (e.g., having numeric and/or graphical display features);

displaying indicators of a trend (e.g., a directional arrow, up, down or flat).

Figure 2:
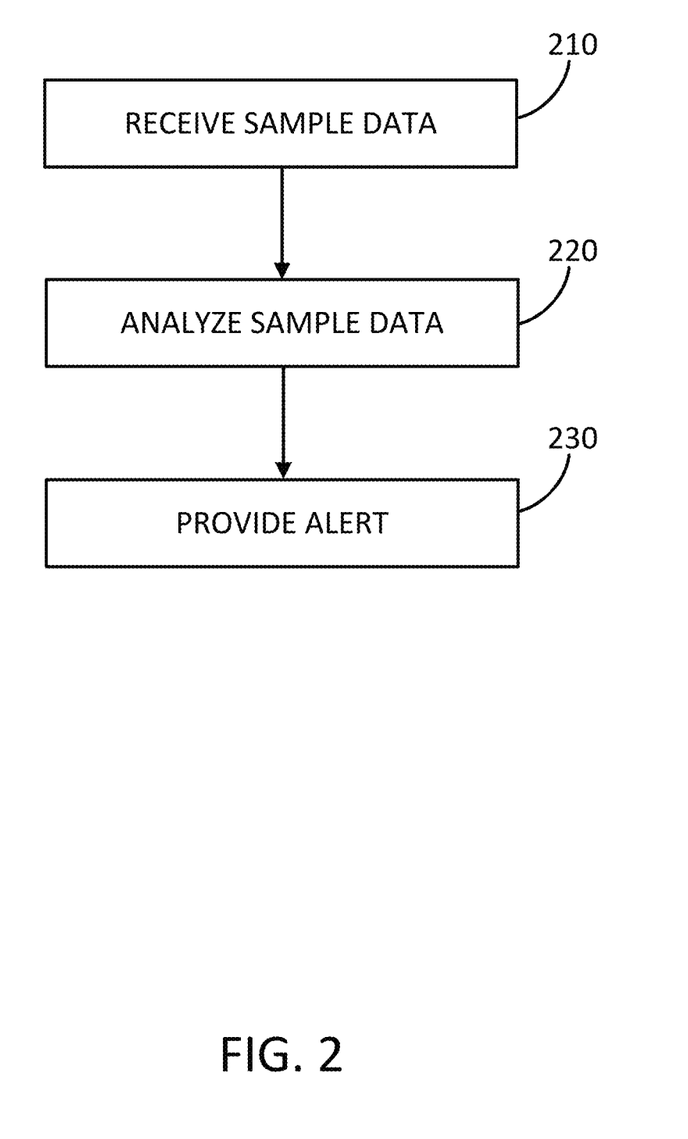
FIG. 2 is a representative schematic of a method described herein.

FIG. 2 represents one of a number of methods described herein, in which, as an example, sample data 20 (as sample data 20a or 20b) from the reading device 10 is received by the indicator module 70 in step 210. The sample data 20 may be received, for example, in an automated cycle, in which sample data is received in accordance with a test sequence having a specified sampling time (e.g., every 30 seconds), for a specified duration (e.g., for 5 minutes), and is configured with a repeat function, for example, to repeat every two hours or every four hours. Indicator module 70 analyzes sample data 20 comparing it with a prior sample data, a prior trend, and or providing a rate of change in sample data in step 220 of FIG. 2. Indicator module 70 initiates an alert (e.g., an image, symbol, sound, vibration, light, etc.) in step 230 when the analysis provides a blood glucose value outside an acceptable trend of blood glucose values and/or outside an acceptable rate of change of blood glucose values in step 230 of FIG. 2.

In one or more embodiments, sample data 20 and/or output 90 is graphically displayed in real time or on-demand on the user interface 100. The sample data 20 may be obtained readily and easily, as often or as infrequent as desired.

The system described herein is beneficial in identifying changes in blood glucose, such as when introducing a new insulin protocol, new foods, new exercise or lifestyle changes, or during more challenging lifestyle events (e.g., with strenuous exercise, during testing or other high performance situation), and even when sick or during rest or sleep or when eating.

Figure 3:
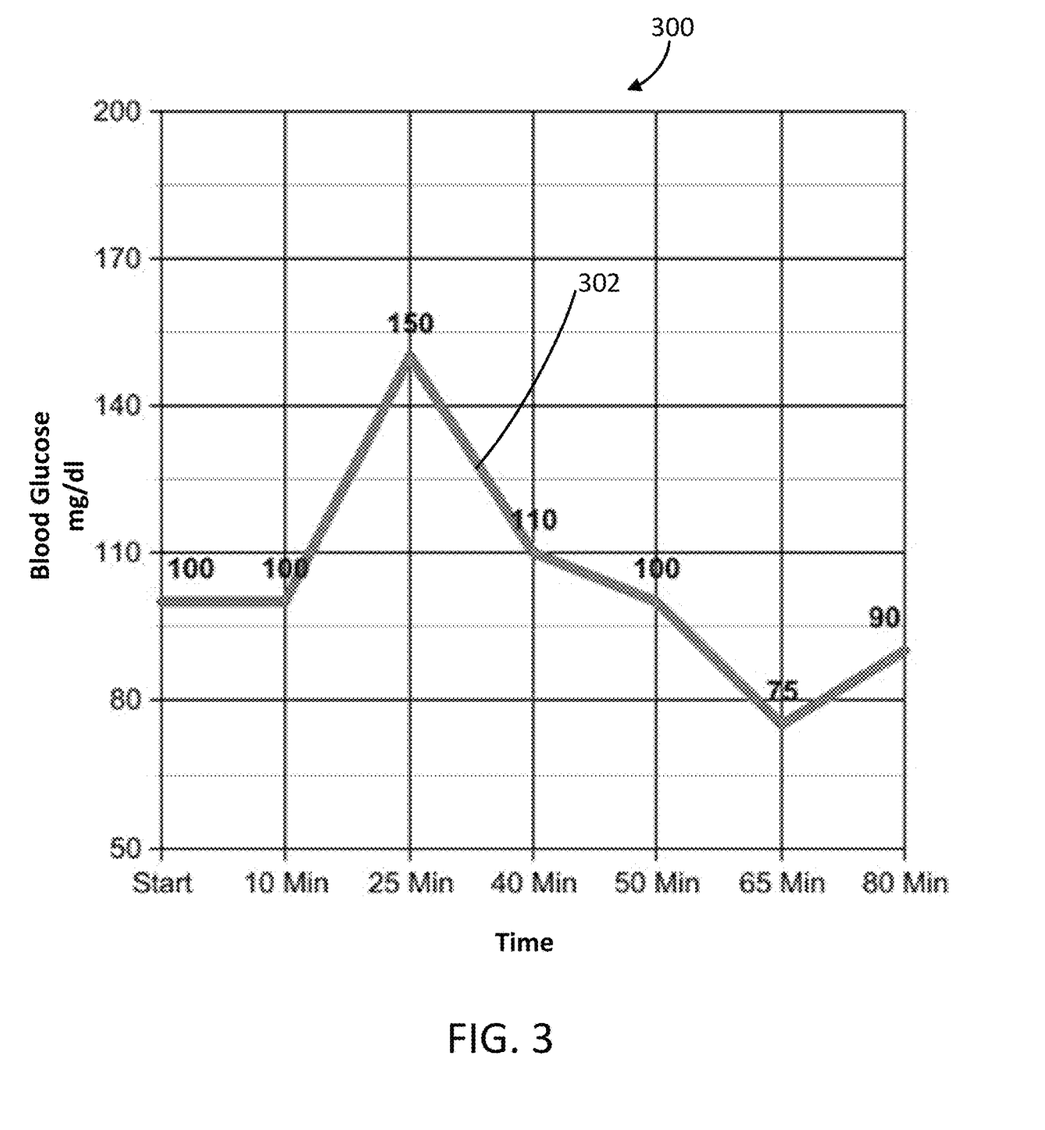
FIG. 3 depicts a chart illustrating an example blood glucose level changing over time.

With reference now to FIG. 3, various beneficial aspects of the system and methods described herein are further discussed. A chart 300 showing an example actual blood glucose value 302 over time of an example individual is provided. Various aspects of the disclosure herein are clarified with reference to a comparison of the results of measuring such an evolution of blood glucose levels with a) a subcutaneous continuous blood glucose meter, b) a strip spot blood glucose meter, and c) the systems and methods disclosed herein.

For example, a subcutaneous continuous blood glucose meter frequently exhibits a lag phenomenon where the measured blood glucose level is out of date because the meter samples subcutaneous tissue rather than a flowing volume of blood. For instance, a 15 minute lag between actual blood glucose levels and trends and the level/trend shown on the meter may be typical. Thus, a reading at 25 minutes would show a blood glucose of 100 mg/dl and flat even though the actual blood glucose at 25 minutes is 150 mg/dl and has been rising which could lead to delays in addressing a high blood glucose condition. This can contribute to long-term health issues. Similarly, a reading at 40 minutes would show a blood glucose of 150 mg/dl and rising although the actual blood glucose is 110 mg/dl and falling which could lead to inappropriate medicating that would accelerate the drop in blood glucose. Furthermore, a reading at 65 minutes would show a blood glucose of 100 mg/dl and falling slowly although the actual blood glucose is 75 mg/dl and dropping rapidly—a dangerous situation that would not be indicated. Finally, blood glucose readings at other points reflected in the chart 300 (or in general of fluctuating blood glucose levels which are typical for many persons with diabetes) create similar challenges to those described above.

Moreover, a strip spot blood glucose meter is associated with less frequent measuring, due to the invasive and/or unpleasant nature of the blood glucose measurement process. Thus, any blood glucose trend information would be developed from very limited data. For example, a spot reading at 10 minutes of 100 mg/dl followed by the next spot reading at 40 minutes of 110 mg/dl would imply a rising blood glucose although the blood glucose level is actually falling, not rising. Similarly, a spot reading at 25 minutes of a blood glucose of 150 mg/dl followed by the next spot reading at 80 minutes of blood glucose of 90 mg/dl would imply a falling blood glucose that would normally be medicated when actually the blood glucose of 90 mg/dl is rising which would normally not be medicated. Moreover, a spot reading at the start followed by a spot reading at 50 minutes would indicate a steady blood glucose of 100 mg/dl when in fact the blood glucose is falling and should be monitored. Finally, blood glucose readings at other points reflected in the chart (or in general of fluctuating blood glucose levels which are typical for many persons with diabetes) create similar challenges to those described above.

In stark contrast to these limitations of various alternative mechanisms, the system and methods described herein provide for operation as follows. For instance, a noninvasive, frequent real-time blood glucose testing with real-time trends via rapid sequential measurements over a short period of time may be implemented so that blood glucose readings at any point reflected in the chart 300 (or in general of fluctuating blood glucose levels which are typical for many persons with diabetes) provides both a real-time spot reading along with the context of whether the blood glucose level is rising, falling, flat or going through a period of change which will enable better blood glucose management decisions. Such information can be provided from spot checks without requiring the device to be attached fulltime. However, it could also function as a continuous blood glucose meter if attached fulltime.

In one or more embodiments, the device and systems described herein may be individualized. For example, the device and systems may be individualized upon establishing a trend specific for an individual. The device and systems described herein provide accurate blood glucose values and/or changes in blood glucose values in real time to said individual and/or may be transmitted wired or wireless to a computer or processing unit remote from the individual and/or from the described device or system.

The present disclosure includes preferred or illustrative embodiments in which specific sensors and methods are described. Alternative embodiments of such sensors can be used in carrying out the invention as claimed and such alternative embodiments are limited only by the claims themselves. Other aspects and advantages of the present invention may be obtained from a study of this disclosure and the drawings, along with the appended claims.

The invention claimed is:

1. A system for obtaining real time blood glucose values comprising:
　an ear-attachable housing comprising a pre-calibrated optical sensor for obtaining real-time blood glucose data corresponding to a real-time glucose level in a flowing volume of blood and not subcutaneous tissue comprising periodic, instantaneous blood glucose samples of the real-time glucose level in the flowing volume of blood and not subcutaneous tissue in real time at periodic intervals by transmitting optical energy through the flowing volume of blood in an ear of an individual without user calibration;
　a monitoring module in electronic communication with the sensor, the monitoring module including:
　a receiving unit for receiving the real-time blood glucose data corresponding to the real-time glucose level in the flowing volume of blood and not subcutaneous tissue in real time from the sensor, and
　an analyzer connected to the receiving unit, wherein the analyzer:
　　(i) receives, from the receiving unit, some or all of the real-time blood glucose data comprising periodic, instantaneous blood glucose samples obtained in real time and corresponding to the real-time glucose level in the flowing volume of blood;
　　(ii) compares in a first comparison some or all of the real-time blood glucose samples,
　　(iii) computes a continuous trend connecting the instantaneous periodic real-time blood glucose samples, wherein the continuous trend comprises (i) a trend direction and (ii) a rate of change of a blood glucose magnitude corresponding to the real-time glucose level in the flowing volume of blood,
　　　wherein the trend direction comprises a presently extant real-time direction of change of the blood glucose magnitude,
　　　wherein the rate of change comprises a presently extant real-time change in the blood glucose magnitude over a first period of time,
　　(iv) identifies the continuous trend as an unacceptable trend;
　　(v) generates, in real-time response to the unacceptable trend, an indicator in real time, wherein the indicator corresponds to a presently extant real-time trend direction of the unacceptable trend;
　a user interface connected to the analyzer and receiving, from the analyzer, the indicator and providing, as an output on the user interface, the indicator,
　wherein the sensor is a source of optical energy comprising:
　　an emitter with an emission pattern to pass optical energy through a portion of the ear and measure the real-time glucose level in the flowing volume of blood in the portion of the ear; and
　　at least one optical detector to receive the optical energy after passage through the portion of the ear and output an optical polarization data corresponding to a polarization of the optical energy representative of a presently extant real-time blood glucose concentration of blood in the portion of the ear, wherein the periodic instantaneous blood glucose samples correspond to the optical polarization data.

2. The system of claim 1, wherein the system further comprises a memory for storing at least a portion of the obtained blood glucose data.

3. The system of claim 1, wherein the sensor and the monitoring module are in one device.

4. The system of claim 1, wherein at least one of the sensor and the system is portable.

5. The system of claim 1, wherein the entire system is wearable.

6. The system of claim 1, wherein the analyzer operates in accordance with preset parameters.

7. The system of claim 1, wherein the receiving unit operates in accordance with preset parameters.

8. The system of claim 1, wherein the analyzer operates in accordance with preset parameters, the preset parameters repeating automatically.

9. The system of claim 1, wherein the receiving unit operates in accordance with preset parameters, the preset parameters repeating automatically.

10. The system of claim 1, wherein the indicator is provided as output on the user interface as at least one of a symbol, a number, and a sound.

11. The system of claim 1, wherein in the analyzer repeats a comparison with new blood glucose data obtained in real time in a second comparison when the blood glucose data is unacceptable in the first comparison.

12. A system for obtaining real time blood glucose values comprising:
- a reading device comprising a detection module including a noninvasive sensor configured to obtain blood glucose data in real time from a flowing volume of blood within an ear of an individual and generate sample data therefrom while the flowing volume of blood is within the ear and the reading device remains completely outside of the ear;
- wherein the detection module comprises an non-invasive ear-attachable pre-calibrated optical sensor for obtaining blood glucose data comprising periodic, instantaneous blood glucose samples in real time at periodic intervals by (i) transmitting optical energy through the ear of the individual without user calibration and (ii) measuring a polarization of the optical energy, wherein the polarization corresponds to a blood glucose concentration of the flowing volume of blood within the ear, and wherein the detection module is configured to continuously receive the real-time blood glucose data from the noninvasive optical sensor,
- wherein the ear-attachable pre-calibrated optical sensor comprises:
  - at least one source of optical energy;
  - at least one detector to detect the optical energy after passage through the flowing volume of blood within the ear;
- a monitoring module configured to continuously receive sample data from the reading device, and in response, to provide a real-time output comprising a trend in blood glucose value based on the periodic, instantaneous blood glucose samples, wherein the sample data is processed continuously,
- wherein the providing the real-time output comprising the trend comprises:
  - computing a continuous trend connecting samples of the sample data, the continuous trend comprising (i) a trend direction and (ii) a rate of change of the blood glucose value,
  - wherein the trend direction comprises a direction of change of the blood glucose value,
  - wherein the rate of change comprises a change in magnitude of the blood glucose value over a first period of time,
  - wherein the real-time output comprises an indication that the continuous trend is an unacceptable trend,
  - wherein the indication corresponds to a representation of the trend direction of the unacceptable trend.

13. The system for obtaining real time blood glucose values according to claim 12, wherein an output module provides continuous real-time output.

14. The system for obtaining real time blood glucose values according to claim 12, wherein an output module provides an indicator in response to one or more blood glucose values being outside a range of specified values.

15. The system for obtaining real time blood glucose values according to claim 12, wherein an output module provides an indicator in response to a trend of blood glucose values exceeding a rate of change of a glucose level specific for the user.

16. The system for obtaining real time blood glucose values according to claim 12, further comprising a database storing relational data comprising an average rate of change of blood glucose over a fixed number of samples of the sample data.

17. A method of obtaining real time blood glucose values comprising:
- receiving sample data comprising periodic, instantaneous blood glucose samples from a reading device, by an indicator module of a monitoring module associated with the reading device,
- wherein the reading device comprises an ear-attachable housing comprising a pre-calibrated optical sensor for obtaining the sample data comprising the periodic, instantaneous blood glucose samples, in real time and at periodic intervals, by (i) transmitting optical energy through an ear of an individual, without user calibration and (ii) measuring a polarization of the optical energy, wherein the polarization corresponds to a blood glucose concentration of blood inside a tissue of the ear;
- analyzing, by the monitoring module in electronic communication with the sensor, the sample data by comparing the sample data with at least one of a prior trend of prior sample data, the prior trend comprising (i) a direction of a change of blood glucose concentration, (ii) a magnitude of the change of the blood glucose concentration, and (iii) a duration of time associated with the change of the blood glucose concentration; and
- indicating by the indicator module an alert in response to the analyzing step providing a blood glucose value outside an acceptable magnitude of change of the blood glucose concentration and outside an acceptable rate of change of the blood glucose concentration, wherein rate of change comprises the magnitude of change divided by the duration of time.

* * * * *